United States Patent
Brouet

(10) Patent No.: US 10,485,938 B2
(45) Date of Patent: Nov. 26, 2019

(54) PROCESS FOR THE SURFACE TREATMENT OF A METERING VALVE

(71) Applicant: APTAR FRANCE SAS, Le Neubourg (FR)

(72) Inventor: Guillaume Brouet, Rouen (FR)

(73) Assignee: APTAR FRANCE SAS, Le Neubourg (FR)

( * ) Notice: Subject to any disclaimer, the term of this patent is extended or adjusted under 35 U.S.C. 154(b) by 833 days.

(21) Appl. No.: 14/777,552

(22) PCT Filed: Mar. 18, 2014

(86) PCT No.: PCT/FR2014/050620
§ 371 (c)(1),
(2) Date: Sep. 16, 2015

(87) PCT Pub. No.: WO2014/147331
PCT Pub. Date: Sep. 25, 2014

(65) Prior Publication Data
US 2016/0279353 A1    Sep. 29, 2016

(30) Foreign Application Priority Data
Mar. 19, 2013  (FR) ...................... 13 52433

(51) Int. Cl.
*A61M 11/00* (2006.01)
*B05D 5/08* (2006.01)
*B05D 7/00* (2006.01)
*A61M 39/22* (2006.01)
*C25D 9/02* (2006.01)
*B05D 1/36* (2006.01)

(52) U.S. Cl.
CPC .......... *A61M 11/007* (2014.02); *A61M 39/22* (2013.01); *B05D 5/08* (2013.01); *B05D 7/52* (2013.01); *B05D 7/54* (2013.01); *C25D 9/02* (2013.01); *A61M 2207/00* (2013.01); *B05D 1/36* (2013.01)

(58) Field of Classification Search
CPC ....................... A61M 11/007; A61M 2207/00; A61M 39/22; B05D 5/08; B05D 7/52; B05D 7/54
See application file for complete search history.

(56) References Cited

U.S. PATENT DOCUMENTS

| | | | |
|---|---|---|---|
| 2003/0089368 A1* | 5/2003 | Zhao ................... | A61M 15/009 128/200.23 |
| 2004/0035417 A1* | 2/2004 | Ottolangui ............ | B65D 83/38 128/202.17 |
| 2004/0071906 A1* | 4/2004 | Brewis ..................... | C08J 7/065 428/35.7 |
| 2004/0134824 A1* | 7/2004 | Chan ...................... | B65D 83/38 206/524.1 |
| 2004/0223916 A1* | 11/2004 | Burt ....................... | A61K 9/008 424/45 |
| 2005/0129620 A1* | 6/2005 | Clark ....................... | C08J 7/047 424/45 |
| 2005/0201945 A1* | 9/2005 | Bonvoisin ................ | B05D 1/62 424/45 |
| 2013/0022750 A1* | 1/2013 | Bruna ............... | A61M 15/0045 427/407.2 |
| 2017/0152396 A1* | 6/2017 | Jinks .................... | C09D 171/00 |

FOREIGN PATENT DOCUMENTS

| | | |
|---|---|---|
| EP | 0 338 418 A1 | 10/1989 |
| WO | 2008/078052 A2 | 7/2008 |
| WO | 2010/112610 A2 | 10/2010 |
| WO | 2011/077055 A1 | 6/2011 |
| WO | 2011/077056 A1 | 6/2011 |
| WO | 2013/106588 A1 | 7/2013 |

OTHER PUBLICATIONS

International Search Report for PCT/FR2014/050620 dated Jul. 9, 2014.
International Preliminary Report on Patentability for PCT/FR2014/050620 dated May 19, 2016.

* cited by examiner

*Primary Examiner* — Ellen M McAvoy
(74) *Attorney, Agent, or Firm* — Sughrue Mion, PLLC

(57) ABSTRACT

Surface treatment process of a metering valve, said metering valve comprising a valve body and a valve sliding in said valve body, said process comprising a first step of forming a thin film of silicone by chemical grafting on at least one support surface of said valve body and/or said valve, and a second step of applying free silicone on said thin film of grafted silicone, such that said treated support surface simultaneously comprises grafted silicone and free silicone, siloxane chains of the grafted silicone and free silicone associating chemically together to reinforce the holding of the free silicone on said thin film of grafted silicone.

9 Claims, No Drawings

PROCESS FOR THE SURFACE TREATMENT OF A METERING VALVE

CROSS REFERENCE TO RELATED APPLICATIONS

This application is a National Stage of International Application No. PCT/FR2014/050620 filed Mar. 18, 2014, claiming priority based on French Patent Application No. 1352433 filed Mar. 19, 2013, the contents of all of which are incorporated herein by reference in their entirety.

The present invention relates to a surface treatment process for metering valves.

Metering valves operate with propellant gases and are used in particular in distribution devices of fluid product of MDI ("Metered Dose Inhaler") type.

Distribution devices of fluid products of MDI type are well known. They generally comprise a reservoir on which is assembled a metering valve comprising a valve chamber, defining the dose to be distributed at each actuation, and a valve moving in said metering chamber during actuation. Controlling friction of the valve, which can cause malfunctioning of the valve, is a major challenge. In the pharmaceutical field in particular, the risks of malfunctioning of the valve can be critical, for example for critical treatment such as asthma. Any blockage or seizure of the valve due to friction is potentially harmful.

It is known to limit this risk in particular by depositing silicone, in particular dimethylpolysiloxane, onto the components subject to friction. This deposit of free silicone can be done by different techniques, such as buffering for example. This mode of lubrication by deposit of silicone has some disadvantages. Therefore, the holding of the silicone is limited, in particular during filling operation of the fluid product via the valve, where a substantial percentage of this silicone is entrained (effect called washing or "karcher" effect). Also, holding of silicone on lubricated surfaces is not guaranteed over time, and this can result in malfunctioning on completion of a certain period.

It has also been proposed to chemically graft silicone onto surfaces to be treated. Documents WO 2010/112610, WO 2011/077055 and WO 2011/077056 in particular describe such a process. Yet the efficacy of this surface treatment is not optimal, and has proven to be potentially insufficient to guarantee the reliability of the metering valves.

Other existing surface treatment processes also have disadvantages. So, some processes are usable on planar surfaces only. Other processes impose a limited choice of substrate. Polymerization of molecules caused by plasma is complex, costly, and the coating layer obtained is difficult to control and presents problems of ageing. Similarly, polymerization of molecules caused by ultraviolet is also complex and costly, and functions only with photosensitive molecules. The same applies to atom transfer radical polymerization (ATRP), which is also complex and costly. Finally, electro-grafting processes are complex and require conductive support surfaces.

The aim of the present invention is to propose a surface treatment process which does not repeat the above disadvantages.

Another aim of the present invention is to propose a surface treatment process which improves the reliability of metering valves by limiting or eliminating the risks of valve blockage of the valve.

In particular, the aim of the present invention is to provide a surface treatment process which is efficacious, durable and simple to carry out.

The object of the present invention accordingly is a surface treatment process of a metering valve, said metering valve comprising a valve body and a valve sliding in said valve body, said process comprising a first step of forming by way of chemical grafting a thin film of silicone on at least one support surface of said valve body and/or said valve, and a second step of applying free silicone to said thin film of grafted silicone, such that said treated support surface simultaneously comprises grafted silicone and free silicone, siloxane chains of grafted silicone and free silicone associating chemically together to reinforce the holding of the free silicone on said thin film of grafted silicone.

Advantageously, said grafting step comprises the contacting of said surface in contact with the fluid product with a solution comprising at least one adhesion primer, said adhesion primer being a cleavable aryl salt and at least one monomer or a polymer selected from the group consisting of vinyl- or acrylic-terminated siloxanes.

Advantageously, vinyl- or acrylic-terminated siloxanes are selected from the group consisting of vinyl- or acrylic-terminated polyalkylsiloxanes such as vinyl- or acrylic-terminated polymethylsiloxane, vinyl- or acrylic-terminated polydimethylsiloxane such as polydimethylsiloxane-acrylate (PDMS-acrylate), vinyl- or acrylic-terminated polyarylsiloxanes such as vinyl- or acrylic-terminated polyphenylsiloxane such as polyvinylphenylsiloxane, vinyl- or acrylic-terminated polyarylalkylsiloxanes such as vinyl- or acrylic-terminated polymethylphenylsiloxane.

Advantageously, cleavable aryl salt is selected from the group consisting of diazonium aryl salts, ammonium aryl salts, phosphonium aryl salts, sulfonium aryl salts and iodinium aryl salts.

Advantageously, said thin film of grafted silicone has a thickness of less than 1 micrometer, preferably between 10 and 2000 angstroms.

Advantageously, said second step of applying free silicone is conducted by buffering.

Advantageously, said metering valve is fixed on a reservoir containing the fluid product to be distributed and propellant gas to form a distribution device of fluid product of the type MDI.

Advantageously, said distribution device comprises a dose counter for counting the number of distributed doses or remaining to be distributed from said distribution device.

Advantageously, said fluid product is a liquid pharmaceutical product intended in particular to be sprayed orally.

According to the invention, a silicone-grafting step is associated with a deposit step of free silicone, that is, a non-grafted silicone. Lubrication of the surface of treated components is accordingly achieved by means of a layer of a vinyl-terminated silicone grafted onto said surface (grafted silicone), and additional deposit of non-grafted silicone (free silicone). The free silicone can be different to the grafted silicone, but preferably these two silicones are identical to that usually used in pharmaceutical industry (dimethylpolysiloxane), in particular to conserve the same characteristics of chemical compatibility in contact with the active ingredient in the reservoir. An advantage of depositing free silicone identical to that already usually used is that its behaviour in contact with fluid and active ingredient, which can happen for example in the event of partial migration in the reservoir, is known. This simplifies respecting regulatory requirements, in particular concerning compatibility with the active product.

The holding of free silicone on the layer of grafted silicone is improved by a chemical phenomenon of association of siloxane chains of the grafted silicone and free silicone together. This phenomenon occurs to minimise the total surface energy of the silicone.

Therefore, the invention improves the siliconizing of valves, and accordingly boosts their reliability. In particular, it reduces or even eliminates the risks of malfunctioning of the valve in particular with a view to emptying, that is, when there is no longer enough silicone at the surface to ensure the preferred lubrication function, or when force resistant to the rise of the valve risks perturbing its operation, for example in the event of adding a counter to the valve in the MDI device.

Grafted Silicone:

For the grafting step, a process similar to that described in document WO 2008/078052 can be used, which describes a preparation process of an organic film on the surface of a solid support in non-electrochemical conditions. This type of process has proven adapted to form an anti-friction thin film on moving surfaces during actuation of the above distribution devices.

The aim of the process is to synthetically prepare a thin film of silicone at the surface of the valve body and/or of the valve of the valve. This process mainly comprises contacting of said support surface with a liquid solution. The latter comprises at least one solvent and at least one adhesion primer enabling formation of radical entities from the adhesion primer.

The thin film of silicone is covalently bonded to the surface of the support on which the process is performed. According to the thickness of the film, its cohesion is ensured by the covalent bonds which develop between the different units.

The solvent employed within the scope of the process can be protic or aprotic. It is preferable that the primary is soluble in said solvent.

"Protic solvent" means a solvent which comprises at least one atom of hydrogen likely to be liberated in the form of proton. The protic solvent can be selected from the group consisting of water, deionised water, distilled water, acidified or not, acetic acid, hydroxylated solvents such as methanol and ethanol, liquid glycols of low molecular weight such as ethylene glycol, and mixtures thereof. In a first variant, the protic solvent only consists of a protic solvent or a mixture of different protic solvents. In another variant, the protic solvent or the mixture of protic solvents can be used as a mixture with at least one aprotic solvent, given that the resulting mixture has the characteristics of a protic solvent. Acidified water is the preferred protic solvent and, more particularly, acidified distilled water or acidified deionised water.

"Aprotic solvent" means a solvent which is not considered as protic. Such solvents are not likely to release a proton or accept one in non-extreme conditions. The aprotic solvent is selected advantageously from dimethylformamide (DMF), acetone and dimethyl sulfoxyde (DMSO).

The term "adhesion primer" corresponds to any organic molecule likely in some conditions to be chemically absorbed to the support surface by radical reaction such as radical chemical grafting. Such molecules comprise at least one functional group likely to react with a radical and also a reactive function vis-a-vis another radical after chemisorption. These molecules are capable of forming a film of polymeric nature after grafting a first molecule onto the surface of the support then reaction with other molecules present in its environment.

The term "radical chemical grafting" refers in particular to use of molecular entities having an unpaired electron to form bonds of covalent bond type with the support surface, said molecular entities being generated independently of the support surface on which they are intended to be grafted. In this way, the radical reaction results in formation of covalent bonds between the pertinent support surface and the derivative of the grafted adhesion primer then between a grafted derivative and molecules present in its environment.

"Derivative of the adhesion primer" means a chemical unit resulting from the adhesion primer, after the latter has reacted by radical chemical grafting in particular with the support surface, or with another radical. It is clear for the skilled person that the reactive function vis-a-vis another radical after chemisorption of the derivative of the adhesion primer is different to the function involved in the covalent bond, in particular with the support surface. The adhesion primer is preferably a cleavable aryl salt selected from the group consisting of diazonium aryl salts, ammonium aryl salts, phosphonium aryl salts, sulfonium aryl salts and iodinium aryl salts.

The cleavable aryl salts are selected from compounds of general formula $ArN_2^+, X^-$ in which Ar represents the aryl group and $X^-$ represents an anion. The aryl group in an organic compound is a functional group deriving from an aromatic core.

In an embodiment, the anions $X^-$ are selected from inorganic anions such as halogenides, such as $I^-$, $Cl^-$ and $Br^-$, halogenoborates such as tetrafluoroborate and organic anions such as alcoolates, carboxylates, perchlorates and sulfonates.

In an embodiment, the aryl groups Ar are selected from aromatics or heteroaromatics, optionally mono- or polysubstituted, comprising one or more aromatic cycles of 3 to 8 carbons. The heteroatoms of the heteroaromatic compounds are selected from N, O, P and S. The substituents can contain alkyl groups and one or more heteroatoms such as N, O, F, Cl, P, Si, Br or S.

In an embodiment, aryl groups are selected from aryl groups substituted by attractor groups such as $NO_2$, COH, CN, $CO_2H$, ketones, esters, amines and halogens.

In an embodiment, the aryl groups are selected from the group consisting of the phenyl and the nitrophenyl.

In an embodiment, the cleavable aryl salt is selected from the group consisting of phenyldiazonium tetrafluoroborate, 4-nitrophenyldiazonium tetrafluoroborate, 4-bromophenyldiazonium tetrafluoroborate, 4-aminophenyldiazonium chloride, 4-aminomethylphenyldiazonium chloride, 2-methyl-4-chlorophenyldiazoniom chloride, 4-benzoylbenzenediazonium tetrafluoroborate, 4-cyanophenyldiazonium tetrafluoroborate, 4-carboxyphenyldiazonium tetrafluoroborate, 4-acetamidophenyldiazonium tetrafluoroborate, 4-phenylacetic acid diazonium tetrafluoroborate, 2-methyl-4-[(2-methylphenyl)diazenyl]benzenediazonium sulfate, 9,10-dioxo-9,10-dihydro-1-anthracenediazonium chloride, 4-nitronaphtalenediazonium tetrafluoroborate and naphtalenediazonium tetrafluoroborate.

In an embodiment, cleavable aryl salt is selected from the group consisting of 4-nitrophenyldiazonium tetrafluoroborate, 4-aminophenyldiazonium chloride, 2-methyl-4-chlorophenyldiazonium chloride, 4-carboxyphenyldiazonium tetrafluoroborate.

In an embodiment, the concentration of cleavable aryl salt is comprised between $5.10^{-3}$ M and $10^{-1}$ M.

In an embodiment, the concentration of cleavable aryl salt is of the order of $5.10^{-2}$ M.

In an embodiment, the cleavable aryl salt is prepared in situ.

Advantageously, said chemical grafting step is initiated by chemical activation of a diazonium salt to form an anchoring layer for said thin film.

Advantageously, said chemical grafting step is initiated by chemical activation.

In an embodiment said chemical activation is initiated by the presence of a reducer in the solution.

In an embodiment the solution comprises a reducer agent.

Reducer agent means a compound which during oxydoreduction reaction gives off electrons. According to an aspect of the present invention, the reducer agent has an oxydoreduction potential whereof the difference in potential relative to the oxydoreduction potential of the cleavable aryl salt is between 0.3 V and 3 V.

According to an aspect of the invention, the reducer agent is selected from the group consisting of reducer metals which can be in the finely divided form such as iron, zinc, or nickel, and a metallic salt which can be in the form of metallocene and an organic reducer such as hypophosphorous acid, ascorbic acid.

In an embodiment, the concentration of reducer agent is comprised between 0.005 M and 2 M.

In an embodiment, the concentration of reducer agent is of the order of 0.6 M.

In an embodiment, said thin film has a thickness less than 1 micrometer, between 10 and 2000 angstroms, advantageously between 10 and 800 angstroms, preferably between 400 and 1000 angstroms. No conventional coating technique produces such chemically grafted thin layers.

Vinyl- or acrylic-terminated siloxane means a saturated hydride of silicon and oxygen formed from straight or branched chains, alternating atoms of silicon and oxygen comprising vinyl units or terminal acrylic units.

In an embodiment vinyl- or acrylic-terminated siloxanes are selected from the group consisting of the vinyl- or acrylic-terminated polyalkylsiloxanes such as vinyl- or acrylic-terminated polymethylsiloxane, vinyl- or acrylic-terminated polydimethylsiloxane such as polydimethylsiloxane-acrylate (PDMS-acrylate), vinyl- or acrylic-terminated polyarylsiloxanes such as vinyl- or acrylic-terminated polyphenylsiloxane such as polyvinylphenylsiloxane, vinyl- or acrylic-terminated polyarylalkylsiloxanes such as vinyl- or acrylic-terminated polymethylphenylsiloxane.

In an embodiment a difference in potential is applied in said solution.

Difference in potential means the difference in potential of oxydoreduction measured between two electrodes.

In an embodiment, the difference in potential is applied by a generator connected to two electrodes, identical or different, dipping in the solution during the soaking step.

In an embodiment, the electrodes are selected from stainless steel, steel, nickel, platinum, gold, silver, zinc, iron, copper, in pure form or in alloy form.

In an embodiment, the electrodes are made of stainless steel.

In an embodiment, the difference in potential applied by a generator is comprised between 0.1 V and 2 V.

In an embodiment, it is of the order of 0.7 V.

In an embodiment, the difference in potential is generated by a chemical cell.

Chemical cell means a cell composed of two electrodes connected by an ionic bridge. According to the present invention, the two electrodes are selected carefully so that the difference in potential is between 0.1 V and 2.5 V.

In an embodiment, the chemical cell is created between two different electrodes dipping in the solution. In an embodiment, the electrodes are selected from nickel, zinc, iron, copper, silver in pure form or in alloy form.

In an embodiment, the difference in potential generated by the chemical cell is comprised between 0.1 V and 1.5 V.

In an embodiment, the difference in potential is of the order of 0.7 V.

In an embodiment, the electrodes are chemically isolated to avoid any contact between the substrate immersed in the solution and the electrodes also dipped in the solution.

The following example was carried out in a glass vat. Unless expressed otherwise, it was carried out in normal temperature and pressure conditions (around 22° C. at around 1 atm) in ambient air. Unless expressed otherwise, the reagents employed were obtained directly commercially without additional purification. The samples earlier underwent ultrasound wetting in soapy water at 40° C.

EXAMPLE

Grafting of a Poly(Dimethylsiloxane) Film of Parts of a Valve to Lubricate it

Valve means a distribution device of fluid product containing propellant gas, comprising a valve body in which a valve slides.

Sodium dodecyl benzene sulfonate (1.307 g, 0.015 M) was solubilised in 175 mL of milliQ water. Vinyl-terminated poly(dimethylsiloxane) (2.5 g, 10 g/L) was added then the mixture was stirred magnetically to form an emulsion.

4-aminobenzoic acid (3.462 g, $2.5 \cdot 10^{-2}$ mol) was solubilised in a solution of hydrochloric acid (9.6 mL in 20 ml MQ water) and hypophosphorous acid (33 mL, $3.1 \cdot 10^{-1}$ mol). This solution was added to the PDMS emulsion.

10 ml of a solution of $NaNO_2$ (1.664 g, $2.37 \cdot 10^{-2}$ mol) in MQ water and the samples were added to this emulsion: EPDM or Nitrile seals and POM top of valve and a control gold slide.

After 15 minutes of reaction, the samples were removed then rinsed successively in Milli-Q® water, ethanol and hexane.

The presence of PDMS on the gold slide and the other samples was confirmed by IR analyses with the specific bands of PDMS at 1260, 1110 and 1045 $cm^{-1}$.

Free Silicone:

The step of applying free silicone to the support surface comprising grafted silicone can be performed as per the prior art, in particular via buffering, pan coating or the Xdot process.

The buffering first provides depositing silicone onto a surface S, and second placing this imbibed surface S in contact with the part to be siliconized according to appropriate kinematics. The result is transfer or deposit of silicone on the component to be siliconized. This process operates on the principle of a buffer or a brush.

"Pan coating" is a process which provides for distribution of silicone by brewing of the parts. Typically, several parts and silicone are introduced to a closed volume and kinematics are generated over a given period to distribute silicone onto the parts. This process operates on the principle of a truck mixer.

The Xdot process comprises droplets of silicones generated by a nozzle the closing of which can be ensured for example by a piezoelectric element; with the silicone arriving from a pressurised reservoir, the micro-motion made by the piezoelectric blocking generates micro-droplets which are projected by their inertia onto the part to be siliconized. This process operates on the principle of a paint gun.

Various modifications are also possible for a skilled person without departing from the scope of the present invention such as defined by the appended claims.

The invention claimed is:

1. A surface treatment process of a metering valve, said metering valve comprising a valve body and a valve sliding in said valve body, characterized in that said process comprises a first step of forming a thin film of silicone by chemical grafting on at least one support surface of said valve body and/or said valve, and a second step of applying free silicone on said thin film of grafted silicone, such that said treated support surface simultaneously comprises grafted silicone and free silicone, siloxane chains of the grafted silicone and free silicone associating chemically together to reinforce the holding of the free silicone on said thin film of grafted silicone.

2. The process according to claim 1, wherein said grafting step comprises the contacting said surface in contact with the fluid product with a solution comprising at least one adhesion primer, said adhesion primer being a cleavable aryl salt and at least one monomer or a polymer selected from the group consisting of vinyl- or acrylic-terminated siloxanes.

3. The process according to claim 2, wherein vinyl- or acrylic-terminated siloxanes are selected from the group consisting of vinyl- or acrylic-terminated polyalkylsiloxanes such as vinyl- or acrylic-terminated polymethylsiloxane, vinyl- or acrylic-terminated polydimethylsiloxane such as polydimethylsiloxane-acrylate (PDMS-acrylate), vinyl- or acrylic-terminated polyarylsiloxanes such as vinyl- or acrylic-terminated polyphenylsiloxane such as polyvinylphenylsiloxane, vinyl- or acrylic-terminated polyarylalkylsiloxanes such as vinyl- or acrylic-terminated polymethylphenylsiloxane.

4. The process according to claim 2, wherein the cleavable aryl salt is selected from the group consisting of diazonium aryl salts, ammonium aryl salts, phosphonium aryl salts, sulfonium aryl salts and iodinium aryl salts.

5. The process according to claim 1, wherein said thin film of grafted silicone has a thickness less than 1 micrometer, preferably between 10 and 2000 angstroms.

6. The process according to claim 1, wherein said second step of applying free silicone is conducted by buffering.

7. A distribution device of fluid product of the type MDI comprising a metering valve fixed on a reservoir containing fluid product to be distributed and propellant gas, characterized in that at least one support surface of said metering valve is subjected to the process according to claim 1.

8. The device according to claim 7, wherein said distribution device comprises a dose counter for counting the number of distributed doses or remaining to be distributed from said distribution device.

9. The device according to claim 7, wherein said fluid product is a liquid pharmaceutical product intended to be sprayed orally.

* * * * *